United States Patent [19]
Müller et al.

[11] Patent Number: 5,248,755
[45] Date of Patent: Sep. 28, 1993

[54] PROCESS FOR THE PREPARATION OF ASYMMETRICALLY SUBSTITUTED UREAS, CARBAMATES OR THIOCARBAMATES

[75] Inventors: Martin Müller, Traun; Gerhard Stern, Sonnberg; Erich Schulz, Ansfelden; Markus Rössler, Linz, all of Austria

[73] Assignee: Chemie Linz Gesellschaft m.b.H., Linz, Austria

[21] Appl. No.: 958,155

[22] Filed: Oct. 9, 1992

Related U.S. Application Data

[60] Continuation-in-part of Ser. No. 807,606, Dec. 16, 1991, abandoned, and a continuation-in-part of Ser. No. 791,214, Nov. 13, 1991, abandoned, which is a division of Ser. No. 552,696, Jul. 12, 1990, Pat. No. 5,091,553.

[30] Foreign Application Priority Data

| | | |
|---|---|---|
| Jul. 28, 1989 [AT] | Austria | A 1831 |
| Jul. 28, 1989 [AT] | Austria | A 1832 |
| Jul. 28, 1989 [AT] | Austria | A 1833 |
| Jan. 18, 1991 [AT] | Austria | A 111 |

[51] Int. Cl.⁵ .............. C07C 67/36; C07C 333/00; C07C 273/00
[52] U.S. Cl. .............. 558/232; 560/24; 564/57; 564/48; 564/61; 564/64
[58] Field of Search ............ 558/232; 560/24; 564/57, 48, 61, 64

[56] References Cited

U.S. PATENT DOCUMENTS

| | | | |
|---|---|---|---|
| 2,712,491 | 7/1955 | Boatright et al. | 423/365 |
| 2,712,492 | 7/1955 | MacKay et al. | 423/365 |
| 3,077,494 | 2/1963 | Griffith | 260/471 |
| 3,449,406 | 6/1969 | Goodman et al. | 260/482 |
| 3,876,665 | 4/1975 | Cooke et al. | 549/349 |
| 3,882,165 | 5/1975 | Pews et al. | 260/471 |
| 4,377,330 | 3/1983 | Stauffer | 354/25 |
| 4,472,568 | 9/1984 | Rasshofer et al. | 560/24 |
| 4,749,806 | 6/1988 | Tkatchenko et al. | 560/24 |
| 5,078,980 | 1/1992 | Mullner et al. | 423/236 |

FOREIGN PATENT DOCUMENTS

| | | |
|---|---|---|
| 0025548A3 | 3/1981 | European Pat. Off. . |
| 0124704 | 11/1984 | European Pat. Off. . |
| 333350 | 9/1989 | European Pat. Off. . |
| 859012 | 12/1952 | Fed. Rep. of Germany . |
| 1908047 | 9/1970 | Fed. Rep. of Germany . |
| 1768805 | 1/1972 | Fed. Rep. of Germany . |
| 116551 | 12/1975 | Fed. Rep. of Germany . |
| 2937331A1 | 4/1981 | Fed. Rep. of Germany . |
| 3117249A1 | 5/1982 | Fed. Rep. of Germany . |
| 3636190A1 | 4/1988 | Fed. Rep. of Germany . |

OTHER PUBLICATIONS

Liebig's Annalen der Chemie, vol. 364, pp. 129-146 (1909) Houben-Weyl, Methoden der Organischen Chemie. Supplementary Volumes, vol. E4, pp. 181-189 (1983).
Houben-Weyl., vol. 8, pp. 140-143 (1949).
Handbuch der Organischen Chemie, vol. 3, 4th Edition, Berlin, Springer Verlag 1921, pp. 22-23.
CA 109:21501h Isocyanates Derived From Dienes, Their Preparation, and Curable Compositions Therefrom; Waterman et al. Jun. 1988.
CA 72:133406v Poly(Olefin Isocyanates) From Unsaturated Hydrocarbons and Isocyanic Acid; Wirpsza, Apr. 1970.
CA 114:250176s Separation of . . . Acid Mixtures; Muellner et al., p. 172, 1991.

(List continued on next page.)

Primary Examiner—Richard L. Raymond
Assistant Examiner—Brian G. Bembenick
Attorney, Agent, or Firm—Wenderoth, Lind & Ponack

[57] ABSTRACT

Process for the preparation of asymmetrically substituted ureas, carbamates, thiocarbamates or substituted isocyanates by reaction of an adduct of isocyanic acid and a tertiary amine with a primary and secondary amine, an alcohol, a thiol or a compound having one or two non-cumulated olefinic double bonds, and a process for the preparation of N-mono- or N,N-disubstituted ureas by reaction of ammonium isocyanate with a primary or secondary amine in a diluent.

10 Claims, No Drawings

OTHER PUBLICATIONS

CA 111:22839t Kinetics . . . Tertiary Amines; Bacaloglu et al., p. 553, 1988.
CA 106:83705q Separation of the . . . -Dinitrophenylureas; Pirkle et al., p. 529, 1986.
Houben-Weyl, Methoden der organischen Chemie, Erweiterungsund, Folgebande zur vierten Auflage, Band E4, Seiten 362 to 364 (1983).
Organic Synthesis, vol. 31 (1951), pp. 9 to 11.
Stoutland et al., J. of org. chemie, vol. 24, 1959, pp. 818–820.

PROCESS FOR THE PREPARATION OF ASYMMETRICALLY SUBSTITUTED UREAS, CARBAMATES OR THIOCARBAMATES

This application is a continuation-in-part of Ser. No. 07/807,606 filed on Dec. 16, 1991 (abandoned), and is also a continuation-in-part of Ser. No. 07/791,214 filed on Nov. 13, 1991 (abandoned), which is a division of Ser. No. 07/552,696 filed on Jul. 12, 1990, now U.S. Pat. No. 5,091,553.

The present invention relates to the preparation of asymmetrically substituted ureas, carbamates, thiocarbamates and substituted isocyanates by reaction of an adduct of isocyanic acid and a tertiary amine in a diluent with primary or secondary amines, alcohols, thiols or a compound which has one or two non-cumulated olefinic double bonds, and to a process for the preparation of N-mono- or N,N-disubstituted ureas by reaction of ammonium isocyanate with primary or secondary amines.

The preparation of asymmetrically substituted ureas can be carried out according to Liebig's Annalen der Chemie, volume 364, pages 129 to 146 by reaction of pure isocyanic acid with a primary or secondary amine in a solvent.

The preparation of N-mono- or N,N-disubstituted ureas by reaction of isocyanic acid, which is liberated, for example, from potassium isocyanate or sodium isocyanate by means of addition of acid, with primary or secondary amines is known and is described, for example, in Houben-Weyl, Methoden der organischen Chemie (Methods of Organic Chemistry), supplement and follow-up volumes to the 4th edition, volume E4, pages 362 to 364. A detailed example for such a reaction is disclosed in Organic Synthesis, volume 31 (1951), pages 9 to 11, where the reaction of p-bromoaniline with sodium isocyanate in glacial acetic acid/water to give p-bromophenylurea is described. EP-A-0 333 350 describes the preparation of aromatic bis-dialkylureas by reaction of an aromatic diamine with isocyanic acid, which is liberated by acidification of potassium isocyanate, sodium isocyanate or silver isocyanate.

Carbamates can be prepared according to Houben-Weyl, Methoden der organischen Chemie (Methods of Organic Chemistry), Supplementary volumes, Volume E4, pages 181 to 189 by reaction of isocyanates with alcohols. It is disclosed in DD 116,551 that isocyanic acid can be reacted with isopropenylbenzene in an organic solvent to give the corresponding isocyanate. However, solutions of free isocyanic acid can only be prepared industrially with difficulty and are difficult to handle so that they can only be employed on the large scale to a limited extent and the isocyanic acid must be liberated from isocyanates for the reaction, polymerization reactions easily occurring.

It has now been found that on addition of primary or secondary amines, alcohols, thiols or compounds which contain one or two non-cumulated olefinic double bonds to a solution or suspension, of an adduct of isocyanic acid with a tertiary amine, which is relatively simple to obtain industrially, asymmetrically substituted ureas, carbamates, thiocarbamates or substituted isocyanates are obtained, and that primary or secondary amines can be reacted not only with isocyanic acid but also with a salt of isocyanic acid, that is to say with ammonium isocyanate, to give N-mono- or N,N-disubstituted ureas. Unexpectedly, the isocyanic acid does not have to be set free from the adduct and ammonium isocyanate respectively by addition of an acid. The adduct and the ammonium isocyanate respectively behave rather like the free isocyanic acid itself.

The invention therefore relates to a process for the preparation of asymmetrically substituted ureas, carbamates, thiocarbamates or substituted isocyanates, which is characterized in that an adduct of isocyanic acid and a tertiary amine is reacted with a primary or secondary amine, an alcohol, a thiol or a compound containing one or two non-cumulated olefinic double bonds in a diluent which is inert under the reaction conditions, and to a process for the preparation of N-mono- or N,N-disubstituted ureas, which is characterized in that ammonium isocyanate is reacted with a primary or secondary amine in a diluent.

Suitable adducts of isocyanic acid and a tertiary amine are substituted ammonium isocyanates of the formula $R_1R_2R_3N \cdot HNCO$, in which the radicals $R_1$, $R_2$ and $R_3$ denote a cyclic amine moiety, such as, for example, N-alkylpyrrolidine, N-alkylpyrrole, N-alkylpiperidine, pyridine, N-alkylmorpholine or $R_1$, $R_2$ and $R_3$ independently of one another denote straight-chain or branched alkyl, aryl, alkylaryl or arylalkyl groups. Straight-chain or branched alkyl groups are, for example, alkyl groups having 1 to 10 C atoms, such as methyl, ethyl, propyl or butyl groups and their isomers, such as iso-propyl, iso-butyl and tert.butyl groups. Aryl, alkylaryl or arylalkyl groups are phenyl groups which are optionally monosubstituted or polysubstituted by straight-chain or branched alkyl groups having 1 to 5 C atoms and which can be connected to the nitrogen atom via either an aromatic or an aliphatic carbon atom. Examples of such groups are phenyl, tolyl, dimethylphenyl, tremethylphenyl, ethylphenyl, isopropylphenyl, benzyl, methylbenzyl or ethylenephenyl groups. Preferred adducts are those with tertiary amines of the general formula $NR_1R_2R_3$ in which $R_1$, $R_2$ and $R_3$ are identical and denote an alkyl group. Particularly preferred here are alkyl groups having 1 to 5 C atoms, for example trimethylamine, triethylamine, tripropylamine, tributylamine and triisopentylamine. Tremethylamine, triethylamine and triisopentylamine are very particularly preferred.

The adduct of isocyanic acid and tertiary amine can be prepared, for example, from a gaseous mixture of isocyanic acid and ammonia by adding a tertiary amine to this mixture, which has a temperature of 250° to 600° C., bringing the resulting gaseous reaction mixture into contact with an inert diluent and cooling. The starting material required, the gaseous mixture of isocyanic acid and ammonia, is formed during the thermal decomposition of urea, for example according to EP-A-0,124,704.

Ammonium isocyanate is formed, for example, by rapid gasification of urea and chilling of the reaction gases, for example in accordance with U.S. Pat. No. 2,712,491, or by spraying molten urea into gaseous ammonia at high temperatures and chilling the reaction mixture, for example in accordance with U.S. Pat. No. 2,712,492, and can be prepared in this manner.

For the preparation of the compounds according to the invention, the adduct of isocyanic acid and tertiary amine is first introduced in a diluent which is inert under the reaction conditions at temperatures of about −20° C. to room temperature. A primary or secondary amine, an alcohol, a thiol or a compound which contains one or two non-cumulated olefinic double bonds is then added with stirring.

To carry out the process according to the invention, in the case of ammonium isocyanate as starting material, either ammonium isocyanate is initially introduced into the reaction vessel in a diluent which is inert under the reaction conditions, the mixture is stirred and a primary or secondary amine is added, or the primary or secondary amine is initially introduced into the reaction vessel in a diluent which is inert under the reaction conditions or, if the amine is liquid, without a further additional diluent, in which case the amine can also serve simultaneously as the diluent, the amine is stirred and ammonium isocyanate is added.

Suitable inert diluents are, for example, aliphatic hydrocarbons, such as pentane, hexane, heptane, aromatic hydrocarbons, such as benzene, toluene, xylene, halogenated aliphatic hydrocarbons, such as methylene chloride, chloroform, carbon tetrachloride, ethyl chloride, ethylene chloride, halogenated aromatic hydrocarbons, such as chlorobenzene, trichlorobenzene, ethers, such as diethyl ether, diisopropyl ether, dibutyl ether, ethyl methyl ether, dioxane, carboxamides, such as dimethylformamide, N-methylpyrrolidone or mixtures of abovementioned diluents.

In the case of ammonium isocyanate additionally as starting material, alcohols, such as methanol, ethanol or diisopropyl alcohol, and water or mixtures of such diluents can be used. Aromatic hydrocarbons, halogenated aliphatic hydrocarbons and carboxamides are preferred, and toluene, chloroform or N-methylpyrrolidone are particularly preferred for the case of an adduct of isocyanic acid and a tertiary amine as starting material, and for the case of ammonium isocyanate aliphatic and aromatic hydrocarbons, halogenated aliphatic or aromatic hydrocarbons, ethers, alcohols and water are preferred, and n-hexane, chloroform, chlorobenzene, dioxane and water are particularly preferred.

Primary and secondary amines are to be understood as meaning those compounds which have one or more amino groups. They may optionally be substituted by other groups which are inert under the reaction conditions. Examples of these are aliphatic, cycloaliphatic or cyclic amines, such as methylamine, ethylamine, hexylamine, hexadecylamine, isopropylamine, isobutylamine, isooctylamine, methylethylamine, cyclohexylamine, pyrrolidine, pyrrole, piperidine, morpholine or dimethylamine, diethylamine, diisopropylamine, ethylenediamine, hexamethylenediamine, 4,4'-diaminodicyclohexylmethane or aromatic amines, such as aniline, nitroanilines, chloroanilines, tolylamines, benzylamine, naphthylamines, phenylenediamines, toluylenediamines and 4,4'-diaminodiphenylmethane.

Alcohols or thiols are understood as meaning compounds which have one or more hydroxyl or mercapto groups. They may optionally be substituted by other groups which are inert under the reaction conditions. Examples of such compounds are aliphatic or cycloaliphatic alcohols or thiols, such as methanol, ethanol, propanol, octadecyl alcohol, isopropanol, isooctanol, cyclohexanol, cyclooctanol, ethylene glycol, glycerol, methylmercaptan, ethylmercaptan, isooctylmercaptan, ethanedithiol, thioglycol, or aromatic alcohols or thiols, such as phenol, nitrophenols, chlorophenols, naphthols, benzyl alcohols, resorcinol, thiophenol, bisphenol A, polyester alcohols and polyether alcohols.

Compounds which contain one or more olefinic double bonds which can optionally be substituted by other groups which are inert under the reaction conditions are, for example, aliphatic or cycloaliphatic compounds, such as ethene, propene, butene, pentene, hexene, hexadecene, isopropene, isobutene, isooctene, cyclohexene, butadiene, octadiene, cyclooctadiene, isoprene, terpenes, or aromatic compounds having an olefinic double bond, such as, for example, styrenes, divinylbenzenes, diisopropenylbenzene, naphthylstyrenes and diphenylethylenes.

The amine, the alcohol, the thiol or the olefin may be added as such, as a gas or a liquid, or together with a diluent as described above, which is gaseous or liquid an inert under the reaction conditions. The amine, the alcohol, the thiol or the olefin can be added in an equivalent amount or in an excess to the adduct of isocyanic acid and tertiary amine. However, it may also be expedient to add the isocyanic acid in excess in order to improve the progress of the reaction.

Preferably, 1 to 7, particularly preferably 1 to 3, mole equivalents of amine, alcohol, thiol or olefin are added per mol of the adduct of isocyanic acid and tertiary amine.

In the case of ammonium isocyanate as starting material, ammonium isocyanate can be added as such, or together with a liquid diluent which is inert under the reaction conditions, as described above, and the primary or secondary amine can be added as such, in gaseous or liquid form, or together with a gaseous or liquid diluent which is inert under the reaction conditions, as described above.

The addition is carried out at temperatures of about $-20°$ C. up to the boiling point of the diluent used, preferably at temperatures of about $-10°$ C. to room temperature, particularly preferably at room temperature.

The amine is added here to the ammonium isocyanate in an equivalent amount or in an excess. However, it may also be appropriate to add the ammonium isocyanate in excess, in order to improve the course of the reaction. Apart from the case where the amine is employed simultaneously as the diluent, the ammonium isocyanate and the amine are preferably employed in equivalent amounts.

After completion of the addition of the amine, the alcohol, the thiol or the olefin, or the ammonium isocyanate respectively, the mixture is subsequently stirred at room temperature and/or, if desired, heated up to the reflux temperature of the diluent used in order to complete the reaction. If desired, the reaction is also carried out under pressure, it being possible to use pressures up to 20 bar. After cooling, the compound formed crystallizes out of the diluent and is filtered off, or the diluent is evaporated. If desired, further purification can be carried out in a customary manner, such as, for example, by recrystallization, distillation or chromatography.

In a preferred embodiment, in the case of ammonium isocyanate as starting material, ammonium isocyanate is dissolved or suspended in a diluent which is inert under the reaction conditions, and the equivalent amount of a primary or secondary amine, diluted with the same inert diluent, is added at room temperature, while stirring. When the addition has ended, the mixture is subsequently stirred at room temperature and heated up to the reflux temperature of the diluent used, in order to bring the reaction to completion. After cooling, the precipitate which has separated out is filtered off with suction and if appropriate recrystallized. If water is used as the diluent, the reaction product can also be recrystallized directly from the reaction solution after dilution with water. If no precipitate separates out after the reaction, the solvent is evaporated off and the residue is crystallized and if appropriate recrystallized or purified by chromatography.

In another preferred embodiment, a liquid primary or secondary amine is initially introduced into the reaction vessel simultaneously as the reactant and as the diluent at room temperature, and ammonium isocyanate is added, while stirring. When the addition has ended, the reaction mixture is stirred first at room temperature and then at elevated temperature in order to bring the reaction to completion. When the reaction has ended, the amine is distilled off or removed by chromatography, and if appropriate the residue is purified by crystallization and recrystallization or chromatography.

The process according to the invention yields asymmetrically substituted ureas, carbamates or thiocarbamates or substituted isocyanates in good purity and high yields and thus represents an enrichment of the art.

EXAMPLE 1

Preparation of Triethylammonium Isocyanate 100 g of urea per hour were continuously introduced into a decomposer. The pyrolysis gases were caused to react in a heatable tube at 320° C. with 255 g of triethylamine per hour, which was introduced in gaseous form. The reaction gases were rapidly cooled to room temperature in a scrubber which was operated with chloroform.

Altogether 213 g (3.5 mol) of urea and 544 g (5.4 mol) of triethylamine were introduced.

Triethylammonium isocyanate was obtained in a yield of 66% of theory, dissolved in chloroform, in this way.

IR 2160 cm$^{-1}$ (sharp band)

EXAMPLE 2

14.1 g of dodecylamine (0.076 mol) dissolved in 20 ml of chloroform were added dropwise at room temperature with stirring to 100 ml of a solution of 10 g of triethylammonium isocyanate (0.069 mol) in chloroform, prepared according to Example 1. After completion of the addition, the mixture was subsequently stirred at room temperature for 24 hours and heated to reflux for 1 hour. The solvent was evaporated and the residue was recrystallized from chloroform. 9.45 g, i.e. 60% of theory, of dodecylurea were obtained in this way.

C—H—N analysis:
theoretical: C 68.4%, H 12.3%, N 12.3%
found: C 68.2%, H 12.3%, N 12.3%

EXAMPLE 3

As described in Example 2, but using 4.9 g of iso-propylamine (0.083 mol) and 100 ml of chlorobenzene as the solvent, iso-propylurea was obtained in a yield of 80% of theory after recrystallizing from water.

C—H—N analysis:
theoretical: C 46.7%, H 9.8%, N 27.2%
found: C 47.0%, H 9.6%, N 27.4%

EXAMPLE 4

As described in Example 2, but using 7.0 g of cyclohexylamine (0.071 mol), cyclohexylurea was obtained in a yield of 70% of theory after recrystallizing from water.

C—H—N analysis:
theoretical: C 59.1%, H 9.9%, N 19.7%
found: C 59.2%, H 9.9%, N 19.7%

EXAMPLE 5

6.3 g (0.086 mol) of diethylamine were added dropwise to 50 ml of a solution of 6.2 g (0.043 mol) of triethylammonium isocyanate in chloroform, prepared according to Example 1, in such a way that the temperature did not rise above room temperature. After completion of the addition, the mixture was subsequently stirred at room temperature for 24 hours and then heated under reflux for 30 minutes. The reaction mixture was evaporated and the residue was recrystallized from diisopropyl ether, 3.5 g, i.e. 70% of theory, of diethylurea having a melting point of 69°–71° C. being obtained.

EXAMPLE 6

13.7 g (0.147 mol) of aniline were added dropwise at room temperature with stirring to 100 ml of a solution of 10.6 g (0.0735 mol) of triethylammonium isocyanate in chloroform, prepared according to Example 1. After completion of the addition, the mixture was subsequently stirred at room temperature for 24 hours, after which it was heated to reflux for 30 minutes. The precipitate which was deposited on cooling the reaction mixture was filtered off with suction and washed with a little diethyl ether. A second crystal fraction was obtained by concentrating the mother liquor.

Altogether 6.0 g, i.e. 60% of theory, of phenylurea having a melting point of 143° to 145° C. were obtained.

After recrystallizing a small amount from water the melting point was 146°–148° C.

EXAMPLE 7

10.1 g (0.1084 mol) of aniline, dissolved in 10 ml of chloroform, were added at −10° C. to 100 ml of a solution of 10.1 g (0.0542 mol) of tri-n-propylammonium isocyanate, prepared according to the procedure described in Example 1. After completion of the addition, the mixture was subsequently stirred at room temperature for 24 hours and heated to reflux for 30 minutes. After cooling the reaction mixture phenylurea crystallized out and was filtered off with suction, washed with a little diethyl ether and dried. 4.8 g of phenylurea, which corresponds to 65% of theory, having a melting point of 144° to 146° C. were obtained in this case.

EXAMPLE 8

13.5 g (0.1444 mol) of aniline were added dropwise at room temperature to 160 ml of a solution of 16.5 g (0.0722 mol) of tri-n-butylammonium isocyanate in chloroform, prepared according to the procedure described in Example 1. After completion of the addition, the mixture was stirred at room temperature for 24 hours and then heated to reflux for 30 minutes. After cooling, phenylurea precipitated out and was filtered off with suction, washed with a little diethyl ether and dried. 5.9 g of phenylurea, which corresponds to 60% of theory, having a melting point of 142° to 145° C. were obtained in this case.

EXAMPLE 9

11.8 g (0.1267 mol) of aniline were added dropwise to 130 ml of a solution of 17.2 g (0.0636 mol) of triisopentylammonium isocyanate in chloroform, prepared according to the procedure described in Example 1, in such a way that the temperature did not rise above room temperature. After completion of the addition, the mixture was subsequently stirred at room temperature for 24 hours and then heated to reflux for 30 minutes. After cooling, phenylurea precipitated out and was filtered off with suction, washed with a little ether and dried. 5.1 g of phenylurea, which corresponds to 60% of theory, having a melting point of 143°–145° C. were obtained in this case.

EXAMPLE 10

As described in Example 6, but using diethyl ether as the solvent, phenylurea having a melting point of 146° to 147° C. was obtained in a yield of 50% of theory after recrystallizing from water.

EXAMPLE 11

As described in Example 6, but using 9.4 g of 4-chloroaniline (0.0735 mol) and dimethoxyethane as the solvent, 4-chlorophenylurea was obtained in a yield of 50% of theory.

$^1$H-NMR: 6.8–7.0 (s, broad, —$NH_2$); 7.36 (d, aromat. —CH—); 7.51 (d, aromat. —CH—); 9.0 (s, —NH—).

EXAMPLE 12

1.88 g of ethylenediamine (0.031 mol) were added dropwise at room temperature with stirring to 100 ml of a solution of 10 g of triethylammonum isocyanate (0.069 mol) in 100 ml of N-methylpyrrolidone, prepared according to the procedure described in example 1. After stirring at room temperature for 24 hours, the reaction mixture was heated to reflux for one hour, the solvent was evaporated and the residue was recrystallized from water. 3.4 g, i.e. 75% of theory, of ethylenediurea were obtained in this way.

C—H—N analysis:
theoretical: C 32.9%, H 6.9%, N 38.3%
found: C 32.8%, H 7.0%, N 38.2%

EXAMPLE 13

6.7 g (0.146 mol) of ethanol were added dropwise at room temperature with stirring to 100 ml of a solution of 10.5 g (0.073 mol) of triethylammonium isocyanate in chloroform, prepared according to Example 1, after which the mixture was subsequently stirred at room temperature for 24 hours and then heated to reflux for 1 hour.

The solvent was evaporated and the residue was recrystallized from ethanol, 4.6 g, i.e. 71% of theory, of ethyl carbamate having a melting point of 46°–50° C. being obtained.

EXAMPLE 14

As described in Example 13, but using 26.6 g of 1-hexadecanol (0.11 mol), hexadecyl carbamate was obtained in a yield of 40% of theory after recrystallizing from chloroform.

$^1$H-NMR: 0.89 (t, —$CH_3$); 1.2–1.6 (m, —$CH_2$—); 4.07 (t, —$CH_2$—O—); 7.2 (s, —$NH_2$).

EXAMPLE 15

A solution of 7 g (0.066 mol) of benzyl alcohol in 20 ml of chloroform was added dropwise at room temperature with stirring to 100 ml of a solution of 9.5 g (0.066 mol) of triethylammonium isocyanate in chloroform, prepared according to Example 1, after which the mixture was subsequently stirred at room temperature for 12 hours and heated to reflux for 30 minutes.

The solvent was evaporated and the residue was recrystallized from ethanol. 7.0 g, i.e. 70% of theory, of benzyl carbamate having a melting point of 88°–89° C. were obtained in this case.

EXAMPLE 16

As described in Example 13, but using 10.3 g of 4-chlorophenol (0.080 mol), 4-chlorophenyl carbamate was obtained in a yield of 45% of theory after recrystallizing from methanol/water.

$^1$H-NMR: 5.5 (s, —$NH_2$); 6.8 (d, aryl); 7.2 (d, aryl)

EXAMPLE 17

18.5 g (0.3 mol) of ethylmercaptan, dissolved in 30 ml of chloroform, were added dropwise at 0° C. with stirring to 120 ml of a solution of 28 g (0.2 mol) of triethylammonium isocyanate in chloroform, prepared according to Example 1, after which the mixture was stirred at this temperature for 1 hour and then subsequently stirred at room temperature for 15 hours. After this, the reaction mixture was heated under reflux for 2 hours. The solvent was distilled off. The oily residue remaining crystallized on cooling and was recrystallized from water.

16 g (0.15 mol), i.e. 75% of theory, of S-ethyl thiocarbamate having a melting point of 99°–102° C. were obtained in this way.

EXAMPLE 18

As described in Example 17, but using 63 g of 1-octadecylmercaptan (0.22 mol) dissolved in 30 ml of N-methylpyrrolidone, S-octadecyl thiocarbamate was obtained in a yield of 60% of theory.

C—H—N analysis:
theoretical: C 69.2%, H 11.9%, N 4.3%
found: C 69.0%, H 12.0%, N 4.2%

EXAMPLE 19

As described in Example 17, but using 18.3 g of iso-propylmercaptan (0.24 mol), S-iso-propyl thiocarbamate was obtained in a yield of 70% of theory after recrystallizing from chloroform.

C—H—N analysis:
theoretical: C 40.3%, H 7.5%, N 11.8%
found: C 40.5%, H 7.3%, N 11.8%

EXAMPLE 20

As described in Example 17, but using 11.3 g of ethanedithiol (0.12 mol), 1,2-di(carbamoylthio)ethane was obtained in a yield of 70% of theory after recrystallizing from chloroform.

$^1$H-NMR: 2,91 (—$CH_2$—$CH_2$—); 7,56 (—$NH_2$)
IR: 1650 cm$^{-1}$, 1620 cm$^{-1}$

EXAMPLE 21

100 ml of a solution of 10 g of cyclohexene (0.12 mol) were added dropwise at 0° with stirring to 100 ml of a solution of 64 g of triisopentylammonium isocyanate (0.24 mol) in chloroform, prepared according to example 1, after which the mixture was subsequently stirred at room temperature for 2 hours and the heated to reflux for about 4 hours.

After filtering the resulting cloudy solution, the solvent was distilled off and the residue was distilled at 68° to 73° C., 20 Torr.

7 g of cyclohexyl isocyanate, i.e. 46% of theory, were obtained in this way.

EXAMPLE 22

3 g (0.025 mol) of alpha-methylstyrene were added dropwise with stirring to 100 ml of a suspension of 11.3 g (0.078 mol) of triethylammonium isocyanate in toluene, prepared according to the procedure described in example 1, after which the mixture was subsequently stirred at room temperature for 3 hours and then heated to reflux for about 4 hours.

A solution of alpha,alpha-dimethylbenzyl isocyanate in toluene was obtained in this way.

After distillation at 40° to 45° C., 1 Torr, alpha,alpha-dimethylbenzyl isocyanate was obtained in a yield of 55% of theory with an $n_D^{15}$ of 1.5048.

EXAMPLE 23

100 ml of a solution of 10 g of m-diisopropenylbenzene (0.06 mol) in toluene were added dropwise with stirring at 0° C. to a suspension of 16.22 g of triisopentylammonium isocyanate (0.06 mol) in 150 ml of toluene, prepared according to the procedure described in example 1, after which the mixture was subsequently stirred at room temperature for 3 hours and heated to reflux for 3 hours. A solution of m-tetramethylxylene diisocyanate in toluene was obtained in this way.

After distillation at 90° to 95° C., 0.4 Torr, m-tetramethylxylene diisocyanate was obtained in a yield of 50% of theory with an $n_D^{25}$ of 1.5136.

EXAMPLE 24

10.8 g of ammonium isocyanate (83% pure) (0.15 mol) were suspended in 90 ml of chloroform, 28.1 g (0.15 mol) of dodecylamine, dissolved in chloroform, were added at room temperature, the mixture was stirred for 1 hour and then heated under reflux for 2 hours.

After cooling, the precipitate which had separated out was filtered off with suction and dried.

33.5 g of dodecylurea, that is to say 98% of theory, with a melting point of 102° to 105° C. were obtained by this procedure.

EXAMPLE 25

20.1 g of cyclohexylurea, that is to say 94% of theory, were obtained in the manner described in Example 24,but using 14.9 g of cyclohexylamine (0.15 mol) instead of dodecylamine.

|  | theoretical | found |
| --- | --- | --- |
| C (%) | 59.1 | 59.2 |
| H (%) | 9.9 | 9.9 |
| N (%) | 19.7 | 19.7 |

EXAMPLE 26

13.7 g of isopropylurea, that is to say 89% of theory, were obtained in the manner described in Example 24, but using 8.9 g of isopropylamine (0.15 mol) instead of dodecylamine.

|  | theoretical | found |
| --- | --- | --- |
| C (%) | 46.7 | 47.0 |
| H (%) | 9.8 | 9.6 |
| N (%) | 27.1 | 27.7 |

EXAMPLE 27

6.1 g of ethylenediurea, that is to say 55% of theory, were obtained in the manner described in Example 24,but using 4.5 g of ethylenediamine (0.075 mol) instead of dodecylamine.

|  | theoretical | found |
| --- | --- | --- |
| C (%) | 32.7 | 32.7 |
| H (%) | 6.9 | 7.0 |
| N (%) | 38.1 | 38.2 |

EXAMPLE 28

4.9 g of phenylurea, that is to say 24% of theory, with a melting point of 145°-148° C. were obtained in the manner described in Example 24,but using 14.0 g of aniline (0.15 mol) instead of dodecylamine and water instead of chloroform, the reaction product being recrystallized directly in the reaction solution after addition of water when the reaction had ended.

EXAMPLE 29

7.6 g of phenylurea, that is to say 37% of theory, with a melting point of 145°-148 C. were obtained in the manner described in Example 24, but using 14.0 g of aniline (0.15 mol) instead of dodecylamine.

EXAMPLE 30

13.3 g of ammonium isocyanate (90% pure) (0.2 mol) were added to 18.6 g of aniline (0.2 mol) at room temperature, while stirring. The reaction mixture was stirred at room temperature for one hour and then at 55° to 60° C. for 5 hours. When the reaction had ended, the excess aniline was distilled off and the residue was recrystallized from water.

12.7 g of phenylurea, that is to say 47% of theory, with a melting point of 145°-148° C. were obtained by this procedure.

EXAMPLES 31-32

20 g of ammonium isocyanate (90% pure) (0.3 mol) were suspended or dissolved in 200 g of diluent at room temperature, and a solution of 18.0 g of 1,6-diaminohexane (0.15 mol), dissolved in the same diluent, was added, while stirring. The reaction mixture was stirred at room temperature for one hour and at 55° to 60° C. for 5 hours and cooled. The precipitate which had separated out was filtered off with suction, recrystallized from water and dried.

The diluents shown in Table 1 were used as the diluent. When water was used as the diluent, 600 ml of water were added to the reaction mixture when the reaction had ended and the precipitate which had separated out was recrystallized therein.

The yields of 1,6-hexanediurea with a melting point of 202°-205° C. shown in Table 1 were obtained by this procedure.

The yields of benzylurea given in Table 1 were obtained in the manner described above, but with addition of 32.2 g of benzylamine (0.3 mol) instead of 1,6-diaminohexane.

|  | theoretical | found |
| --- | --- | --- |
| C (%) | 64.0 | 64.0 |
| H (%) | 6.7 | 6.7 |

-continued

|  | theoretical | found |
|---|---|---|
| N (%) | 18.7 | 18.7 |

TABLE 1

|  | % of the theoretical yield of | |
|---|---|---|
| Diluent | 1,6-Hexane-diurea | Benzylurea |
| n-Hexane | 85 | 76 |
| Toluene | 73 | 67 |
| Chlorobenzene | 56 | 56 |
| Tertrahydrofuran | 71 | 79 |
| Dimethoxyethane | 72 | — |
| 1,4-Dioxane | 74 | 72 |
| Ethanol | 20 | — |
| Water | 59 | 56 |

EXAMPLE 33

18.0 g of 1,6-diaminohexane (0.15 mol) were initially introduced into the reaction vessel in 200 ml of water and were heated to a) 50° C. and b) 100° C., while stirring. 20.0 g of ammonium isocyanate (90% pure) (0.3 mol) were dissolved in water and the solution was added dropwise in each case at the stated temperatures, while stirring. When the reaction had ended, 600 ml of water were added to the reaction mixture and the precipitate which had separated out was recrystallized therein, filtered off with suction and dried.

A yield of a) 45% and b) 47% of theory of 1,6-hexanediurea with a melting point of 202°-205° C. was obtained by this procedure.

EXAMPLE 34

14.11 g of ammonium isocyanate (85% pure) (0.2 mol) were suspended in 200 ml of n-hexane, and 48.3 g of dioctylamine (0.2 mol), dissolved in 200 ml of n-hexane, were added. When the addition had ended, the mixture was subsequently stirred at room temperature for one hour and then heated under reflux for two hours. After the reaction mixture had been cooled, a little urea precipitated and was filtered off. The filtrate was subjected to distillation at 100° C. under 0.03 to 0.04 mbar, volatile constituents being removed.

51.0 g of N,N-dioctylurea, that is to say 90% of theory, were obtained in the form of a yellowish oil by this procedure.

|  | theoretical | found |
|---|---|---|
| C (%) | 71.8 | 71.9 |
| H (%) | 12.8 | 12.9 |
| N (%) | 9.8 | 9.8 |

What we claim is:

1. Process for the preparation of asymmetrically substituted ureas, carbamates or thiocarbamates, comprising reacting an adduct of isocyanic acid and a tertiary amine with a primary or secondary amine, an alcohol or a thiol in a diluent which is inert under the reaction conditions.

2. Process according to claim 1, comprising employing as the adduct of isocyanic acid and a tertiary amine, a compound of the formula $R_1R_2R_3N \cdot HNCO$ in which $R_1$, $R_2$ and $R_3$ independently of one another denote a straight-chain or branched alkyl group, or an aryl, alkylaryl or arylalkyl group, or $R_1R_2R_3N$ denotes a cyclic amine moiety.

3. Process according to claim 1, comprising employing an adduct of isocyanic acid and a trialkylamine.

4. Process according to claim 1, comprising employing a non halogenated or halogenated, aliphatic or aromatic hydrocarbon, or a carboxamide as the diluent.

5. Process according to claim 1, comprising employing chloroform, toluene or N-methylpyrrolidone as the diluent.

6. Process according to claim 1, comprising carrying out the reaction at temperatures from −20° C. up to the boiling point of the diluent.

7. Process according to claim 1, comprising beginning the reaction at −10° C. and completing at the boiling point of the diluent.

8. Process according to claim 1, comprising completing the reaction under pressure.

9. Process according to claim 1, comprising the adduct of isocyanic acid and tertiary amine being prepared by reaction of a gaseous mixture of isocyanic acid and ammonia at a temperature of 250° to 600° C. with a tertiary amine and cooling of the gaseous reaction mixture in an inert diluent, the adduct of isocyanic acid and tertiary amine condensing and being separated from gaseous ammonia.

10. Process according to claim 1, comprising the tertiary amine being a trialkylamine.

* * * * *

UNITED STATES PATENT AND TRADEMARK OFFICE
CERTIFICATE OF CORRECTION

PATENT NO. : 5,248,755
DATED : September 28, 1993
INVENTOR(S) : Martin Mullner, et. al.

It is certified that error appears in the above-indentified patent and that said Letters Patent is hereby corrected as shown below:

On the Title page, item [19] "Müller" should read --Mullner-- and item [75] should also read-- Müllner--.

Signed and Sealed this

Twenty-second Day of February, 1994

Attest:

BRUCE LEHMAN

Attesting Officer

Commissioner of Patents and Trademarks